United States Patent [19]

Miller

[11] 4,286,609

[45] Sep. 1, 1981

[54] HOT OIL FINGERNAIL AND CUTICLE TREATMENT

[75] Inventor: Aaron Miller, Northbrook, Ill.

[73] Assignee: Jovan, Inc., Chicago, Ill.

[21] Appl. No.: 949,197

[22] Filed: Oct. 6, 1978

[51] Int. Cl.³ .......................................... A45D 29/20
[52] U.S. Cl. .................................................... 132/75
[58] Field of Search ................ 132/75, 73, 74.5, 73.5; 206/823, 523–524, 524.8, 525–526; 424/61, 70

[56] References Cited

U.S. PATENT DOCUMENTS

| 3,389,195 | 6/1968 | Gianakos et al. | 206/523 |
| 3,480,020 | 11/1969 | Ernest | 132/88.5 |
| 3,489,690 | 1/1970 | Lachampt et al. | 424/61 X |
| 3,887,702 | 6/1975 | Baldwin | 424/61 |

OTHER PUBLICATIONS

Balsam–Sagarin, vol. 2, Cosmetics Science & Technology, Second Edition 1972, pp. 565–567 and 571 relied upon.
Sagarin, Cosmetics Science and Technology, 1957, pp. 857, 776, 711, 710, and 1067 relied upon.

Primary Examiner—G. E. McNeill
Attorney, Agent, or Firm—Laff, Whitesel & Rockman

[57] ABSTRACT

The invention provides a hot oil treatment for fingernails which involves a fingertip soak in a hot oil treatment bath for a period of three to five minutes. Then, the cuticle of the nail is pushed back. The oil treatment bath includes an emulsion formed in hot water from a blended mixture of vegetable and animal oils, emollients, proteins and vitamins. The invention also provides a novel packaging system which both shock-absorbingly cradles a bottle containing the oil treatment and provides a disposable soaking basin.

3 Claims, 6 Drawing Figures

U.S. Patent  Sep. 1, 1981  4,286,609
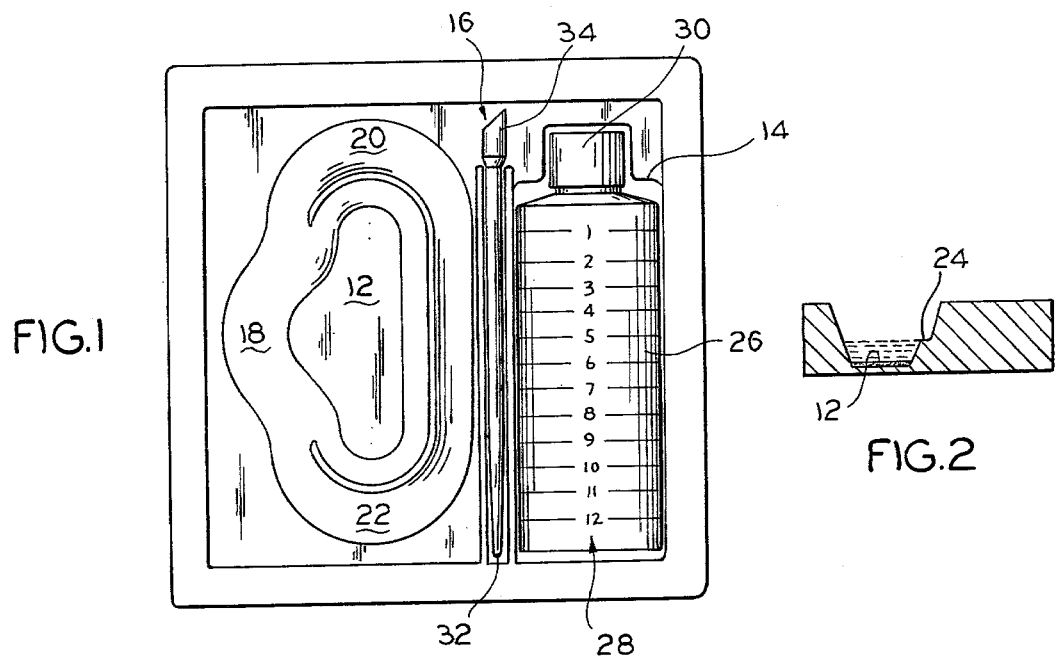
FIG.1
FIG.2
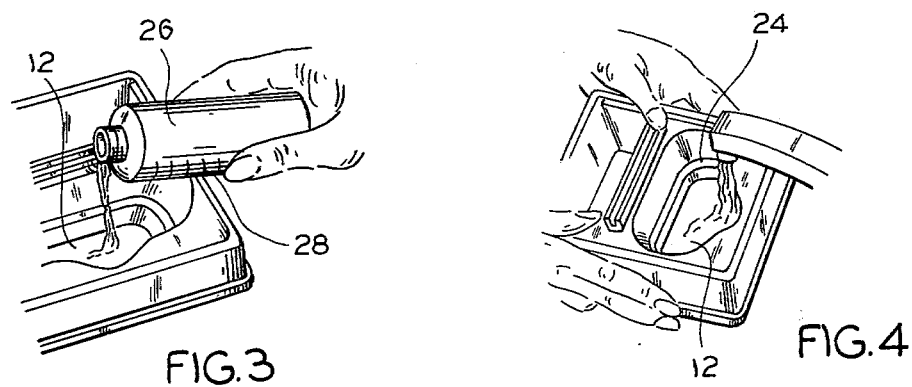
FIG.3
FIG.4
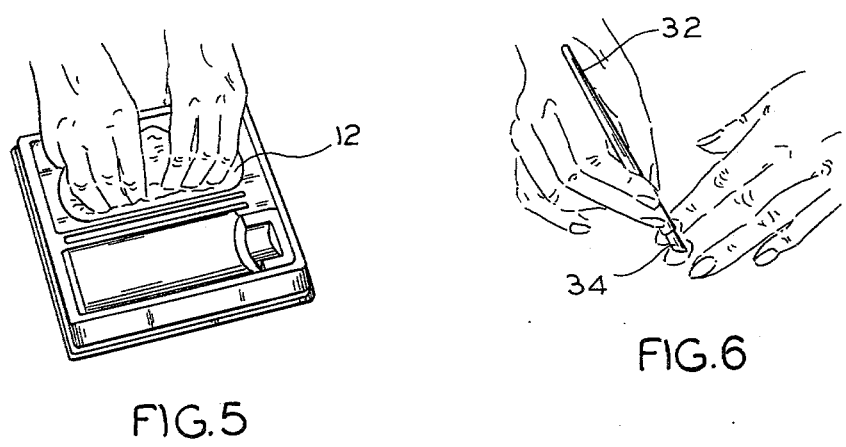
FIG.5
FIG.6

HOT OIL FINGERNAIL AND CUTICLE TREATMENT

This invention relates to complete fingernail treatments and, more particularly, to a blend of oil, to a specially designed packaging and apparatus kit, and to a process to be followed when practicing the inventive process.

There are many different fingernail treatments which range from a purely cosmetic decoration of the nails to an almost complete medicinal treatment. Ideally, such a nail treatment should be both beautifying and medicating; however, these twin goals are difficult to achieve in a single, easy-to-use treatment, having a relative low cost. According to such a treatment, the surface of the nail is made smooth and soft, which is especially good for persons whose nails are dry and brittle. The cuticle is softened and the brittleness of the nail itself is reduced.

Accordingly, an object of the invention is to provide new and improved nail care treatments. Here, an object is to moisturize, smooth, and soften the surface of the nails and of the skin and tissues surrounding the nail.

Another object of the invention is to treat the nails with selected and concentrated vegetable and animal oils, protein, and vitamins. A further object is to provide such treatments in solutions which are free of microbes, harmful chemicals, or allergens.

Yet another object is to provide for such treatments with simple procedures which either are already known to the user or which may be learned with little or no special training. Here, an object is to accomplish the foregoing with simple, low-cost and disposable equipment.

In keeping with an aspect of the invention, these and other objects are accomplished through use of a kit having a formulated hot oil treatment combining concentrated vegetable and animal oils, other emollients, proteins, vitamins and supplementary ingredients such as antioxidants, preservatives, and perhaps perfumes.

The equipment and process used to treat nails according to the invention are shown in the attached drawings wherein:

FIG. 1 is a plan view of a kit having enough hot oil formulated for giving a plurality of treatments (here, twelve treatments), a unique cuticle stick, and a soaking basin;

FIG. 2 is a cross-sectional view of the soaking basin of FIG. 1; and

FIGS. 3–6 illustrate a succession of steps in using the inventive nail treatment process.

To provide a low-cost, disposable kit (FIG. 1) which gives the user everything required to practice the invention, a packaging unit provides both a housing for the kit and a basin for soaking the user's nails. This packaging unit may be a vacuum-formed sheet (for example) having a nail-soaking basin 12 along one edge and a bottle-receiving and cradling support 14 along another edge. In between, the sheet is formed in any suitable manner to retain a cuticle stick 16.

The basin 12 is shaped and proportioned to receive the nails of two human hands, with the thumbs held adjacent each other in a cove 18 and the little fingers in the opposite ends 20,22 of the basin. As best seen in FIG. 2, the basin is formed with an indexing step or ridge 24 around at least part of the perimeter of the basin. This indexing ridge 24 indicates the correct level of hot water to be added when the oil treatment and water are mixed in the proper amounts.

The bottle 26 contains the inventive mixture which is used as a hot oil treatment. Preferably, the bottle is unbreakable; however, an advantage of the cradle 14 in the vacuum-formed sheet is that it provides a shock mount, if a breakable bottle is used. The bottle is marked with a scale at 28 which both designates the required amount of oil mixture that is to be used for each treatment and the amount remaining for future treatments. Preferably, the number of treatments provided along the scale 28 are related to the number of individual treatments that are desirable for a complete program of nail care. Also, the cubic volume of the cap 30 is related to the required amount of oil so that a stated number of capsfull equals the volume of oil indicated by each marking on the scale 28.

The cuticle stick 16 includes any suitable stick means 32 having a preferably soft rubber tip 34. The tip has a generally cylindrical shape with a somewhat slanted end cut in order to give a convenient contour for working and grooming cuticles while they are in a softened state.

The hot oil treatment uses a concentration of vegetable and animal oils, proteins, vitamins and perhaps other ingredients. The type of vegetable and animal oils used in the solution include sesame, olive, mink, soybean, linseed, cottonseed, peanut, corn, tallow and coconut oils. The vegetable oils are all triglycerides. Emulsifying agents which were found to produce desirable results in the treatment include any material having an HLB (hydrophilic lipophilic balance) value of between 7 and 10, such as sorbitans, oleates and stearates. Antioxidants in the formulation can include stearic hydrazide, butylated hydroxytoluene, and butylated hydroxyanisole. Protein is added by including keratin or any amino acid derivative in the treatment.

EXAMPLE

A preferred formula for the hot oil treatment is as follows:

| INGREDIENT | PERCENTAGE RANGE (% w/w) |
|---|---|
| 1. Sesame oil | 0.1–20.0 |
| 2. Olive oil (food grade) | 0.1–20.0 |
| 3. Mink oil | 0.5–20.0 |
| 4. Soybean oil (food grade) | 0.5–20.0 |
| 5. Polyoxyethylene (40) sorbitan peroleate | 1–60.0 |
| 6. Polyoxypropylene (15) stearyl ether | 1–60.0 |
| 7. Raw linseed oil | 1.0–40.0 |
| 8. Cottonseed oil | 1.0–75.0 |
| 9. Butylated hydroxyanisole | 0.05–1.0 |
| 10. propylparaben | 0.05–1.0 |
| 11. Myristoyl hydrolyzed animal protein | 0.1–5.0 |
| 12. Vitamin E (dl-Alpha Tocopheryl acetate) | 0.05–1.0 |
| 13. Vitamin A Palimate | 0.05–1.0 |
| 14. Bronopol (2-Bromo-2-Nitropropane-1, 3-Dial) | 0.01–0.5 |
| 15. Perfume Oil | 0.05–1.0 |

Among the above ingredients, items 1–4, 7 and 8 are emollients which import optimum stability to the formulation when mixed with water. This produces a uniform coating on the nails.

Item 5 is an emulsifying agent which is a mixture of oleic acid esters of sorbitol condensed with an average of 40 moles of ethylene oxide. It is available under the brand name Arlatone T, produced by ICI Americas, Inc., Wilmington, Del.

Item 6 is a combination of an emollient and emulsifier which contributes to the stability of the emulsion formed when water is added. As an emollient, it can be readily rubbed into the skin, lubricating it without excessive oiliness. Although its oiliness is not apparent, it produces the unique effect of reappearance on the skin surface when slight pressure is applied. When it reappears, its lubricious properties again become evident. As a non-volatile solvent, it couples large quantities of perfume oils into mineral oil or other oily cosmetic ingredients. It forms a clear solution in water/alcohol blends over a wide concentration range. It is a polypropylene glycol ether of stearyl alcohol that conforms to the formula:

$$CH_3(CH_2)_{16}CH_2(OCHCH_2)_nOH$$
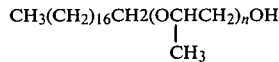

Where: n has an average value of 15. Item 6 is available under the name Arlamol E, produced by ICI Americas, Inc., Wilmington, Del.

Item 9 (CFTA name "BHA") prevents unsaturated fatty materials in the emollients, emulsifiers, and perfume oil from becoming rancid. A food-grade antioxidant offering outstanding compatibility with food fats and substantial carry-through effectiveness which imparts excellent stability to fats, oils, and fat-containing food products. It is a mixture of isomers of tertiary butyl-substituted 4-methoxyphenols, chiefly consisting of 3-tert-butyl-4-hydroxyanisole with lesser amounts of 2-tert-butyl-4-hydroxyanisole which is described as

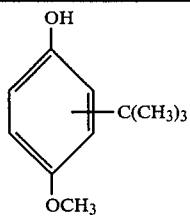

| Molecular weight | 180 |
| Boiling range, 733 mm, °C. | 264–270 |
| Melting range, °C. | 48–55 |

Item 9 is available under the brand name Tenox, produced by Eastman Kodak, Rochester, N.Y.

Item 10 is an anti-microbial agent which enhances shelf life and prevents contamination. It is the organic ester of n-propyl alcohol and p-hydroxy-benzoic acid, described as

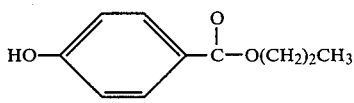

Item 11 is an oil soluble animal protein derivative which is especially well-adapted to condition cuticle, skin, and nail. It is prepared by condensing myristic acid and collagen protein hydrolystate. It is soluble in ethanol, isopropanol, mineral oil, fatty esters such as isopropyl myristate; miscible with petrolalum. This product is used since it adds an emollient feel to the oil treatment and imparts a perceivable conditioning effect to the skin. Item 11 is available under brand name Lexein A240, produced by Inolex Corp., Chicago, Ill.

Item 12 is a vitamin-conditioning agent which is the ester of tocopherol and acetic acid. Item 13 is a vitamin A conditioning agent comprising retinyl palmitate, and is the ester of vitamin A and palmitic acid. Both of these items in combination improve the appearance and feel of the nail and cuticle, and also act as an antioxidant.

Item 14 is 2-Bromo-2-Nitropropane-1,3-Diol, a water soluble, broad spectrum agent highly effective against bacteria and fungi, and an antimicrobial which is particularly effective against Pseudomonas Aeruginosa. It is a substituted aliphatic diol described by the fomula:

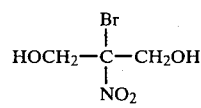

Item 14 is available under the brand name Broponol, produced by Inolex Corporation, Chicago, Ill. It is very water soluble and is unaffected by surface active agents (anionic and non-ionic), proteins or protein hydrolysates at the normally-used levels.

Among the items listed above, the three which are judged most important in combination with the animal and vegetable oils are items 5, 6 and 9 which preferably constitute 7–10% of the total. Of course, the remaining ingredients are also of importance; however, their use is subject to a much greater latitude and discretion.

The above-indicated combination of ingredients produces a conditioning oil for softening the cuticle and reducing the brittleness of the nail. It uses a combination of concentrated vegetable and animal oils, plus other emollients, protein, and vitamins in a form where the oil is water-dispersable. When added to hot water, the fomulation forms an oil-water emulsion. When the nails are dipped in the solution, as will be explained, the effect is similar to placing the nails in a hot emulsified lotion. The nails are moisturized, and the use of hot water in the treatment enhances the moisturizing effect. This treatment has been found effective in producing a smooth and soft nail surface, and in softening the skin around the nail. Thus, the treatment is useful in combating dry skin and brittle nails.

The inventive nail care procedure will be described next. The first step (FIG. 3) is to pour the hot oil treatment from bottle 26 and into the basin 12, according to the scale 28 on the bottle (FIG. 1). Second, hot tap water is introduced into the basin until the level reaches the ledge 24 (FIG. 2). The water and oil are stirred, as required, to mix them and to produce a milky white emulsion. Third, the user immerses the fingertips into the basin 12 (FIG. 5) far enough to completely cover the cuticle and nail area. The fingertips should be soaked for a period of three to five minutes, during which the proteins and the vitamin-enriched oils are absorbed. Fourth, the soft rubber tip 16 of the cuticle stick 32 is dipped into the basin 12 and then used to push back the softened cuticle (FIG. 6). The process should be repeated at least once a week for normal nails, twice a week if the nails are dry and brittle.

Those who are skilled in the art will readily perceive how to modify the invention without departing therefrom. Accordingly, the invention should be construed broadly enough to cover all equivalents falling within the true scope and spirit of the invention.

We claim:

1. A hot oil treatment for conditioning fingernails and cuticles comprising the steps of:
   a. packaging a kit in a combined soaking basin and shock-absorbing container for a combination of components including a bottle of an oil mixture of components used in a bath;
   b. pouring a measured amount of said oil mixture from said bottle into said basin;
   c. pouring hot water into said basin to raise the fluid level within said basin to a predetermined depth;
   d. soaking the tips of the fingers of each hand in said basin for a substantially predetermined period of time adequate to soften the cuticle; and
   e. working the cuticle while it is in the softened state; said oil being a mixture which comprises:

| INGREDIENT | PERCENTAGE RANGE |
|---|---|
| 1. Sesame oil | 0.1–20.0 |
| 2. Olive oil (food grade) | 0.1–20.0 |
| 3. Mink oil | 0.5–20 |
| 4. Soybean oil (food grade) | 0.5–20 |
| 5. Polyoxyethylene (40) sorbitan peroleate | 1.0–10.0 |
| 6. Polyoxypropylene (15) stearyl ether | 1.0–60.0 |
| 7. Raw linseed oil | 1.0–40.0 |
| 8. Cottonseed oil | 1.0–75.0 |
| 9. Butylated hydroxyanisole | 0.05–1.0 |
| 10. Propylparaben | 0.05–1.0 |
| 11. Myristoyl hydrolyzed animal protein | 0.10–5.0 |
| 12. Vitamin E (dl-Alpha Tocopheryl acetate) | 0.5–1.0 |
| 13. Vitamin A Palimate | .05–1.0 |
| 14. Bronopol (2-Bromo-2-Nitropropane-1,3-Diol) | .01–.5 |
| 15. Perfume oil | .05–1.0 |

2. The treatment of claim 1 wherein said container comprises a vacuum-formed sheet having said basin formed along one edge thereof and a bottle-receiving, shock-absorbing cradle formed along another edge thereof, said bottle being marked with a scale for indicating a number of said measured amounts equaling a total program of treatments.

3. A hot oil fingernail and cuticle treatment comprising a hot oil mixture including vegetable and animal oils, emollients, emulsifiers having an HLB value between 7 and 10, proteins, vitamins, which form an emulsion when combined with hot water, said mixture having proportions which soften the skin and cuticle when said fingernails are soaked in said emulsion for a predetermined period of time; and wherein a preferred formula for the hot oil mixture is as follows:

| INGREDIENT | PERCENTAGE RANGE |
|---|---|
| 1. Sesame oil | 0.1–20.0 |
| 2. Olive oil (food grade) | 0.1–20.0 |
| 3. Mink oil | 0.5–20 |
| 4. Soybean oil (food grade) | 0.5–20 |
| 5. Polyoxyethylene (40) sorbitan peroleate | 1.0–10.0 |
| 6. Polyoxypropylene (15) stearyl ether | 1.0–60.0 |
| 7. Raw linseed oil | 1.0–40.0 |
| 8. Cottonseed oil | 1.0–75.0 |
| 9. Butylated hydroxyanisole | 0.05–1.0 |
| 10. Propylparaben | 0.05–1.0 |
| 11. Myristoyl hydrolyzed animal protein | 0.10–5.0 |
| 12. Vitamin E (dl-Alpha Tocopheryl acetate) | 0.5–1.0 |
| 13. Vitamin A Palimate | .05–1.0 |
| 14. Bronopol (2-Bromo-2-Nitropropane-1,3-Diol) | .01–.5 |
| 15. Perfume oil | .05–1.0 |

* * * * *

UNITED STATES PATENT AND TRADEMARK OFFICE
CERTIFICATE OF CORRECTION

PATENT NO. : 4,286,609

DATED : September 1, 1981

INVENTOR(S) : Aaron Miller

It is certified that error appears in the above—identified patent and that said Letters Patent is hereby corrected as shown below:

Col. 2, Line 48, ingredient chart, #5. Percentage Range, "1-60.0" s/b --1-10.00--

Col. 2, Line 57, #14. Chemical Name, "3-Dial" s/b --3-Diol--

Col. 4, Line 21, "Chicago, Ill" s/b --Chicago, Ill--

Signed and Sealed this

Fifth Day of January 1982

[SEAL]

Attest:

GERALD J. MOSSINGHOFF

*Attesting Officer*  *Commissioner of Patents and Trademarks*